(12) United States Patent (10) Patent No.: US 8,673,337 B2
Hutchens et al. (45) Date of Patent: Mar. 18, 2014

(54) METHOD OF TISSUE REPAIR USING A COMPOSITE MATERIAL

(75) Inventors: Stacy A. Hutchens, Knoxville, TN (US); Jonathan Woodward, Solihull (GB); Barbara R. Evans, Oak Ridge, TN (US); Hugh M. O'Neill, Knoxville, TN (US)

(73) Assignees: UT-Battelle, LLC, Oak Ridge, TN (US); University of Tennessee Research Foundation, Knoxville, TN (US)

( * ) Notice: Subject to any disclaimer, the term of this patent is extended or adjusted under 35 U.S.C. 154(b) by 237 days.

(21) Appl. No.: 13/340,114

(22) Filed: Dec. 29, 2011

(65) Prior Publication Data

US 2012/0135086 A1 May 31, 2012

Related U.S. Application Data

(62) Division of application No. 10/295,461, filed on Nov. 15, 2002, now Pat. No. 8,110,222.

(51) Int. Cl.
*A61F 2/00* (2006.01)

(52) U.S. Cl.
USPC ........................................................ 424/423

(58) Field of Classification Search
None
See application file for complete search history.

(56) References Cited

U.S. PATENT DOCUMENTS

| | | | |
|---|---|---|---|
| 5,232,878 A | 8/1993 | Kasuga et al. | |
| 5,626,861 A | 5/1997 | Laurencin et al. | |
| 5,698,265 A | 12/1997 | Mucalo et al. | |
| 5,782,971 A | 7/1998 | Constantz et al. | |
| 5,981,052 A | 11/1999 | Sugiyama | |
| 6,133,170 A | 10/2000 | Suenaga et al. | |
| 6,201,039 B1 | 3/2001 | Brown et al. | |
| 6,300,315 B1 | 10/2001 | Liu | |
| 6,331,312 B1 | 12/2001 | Lee et al. | |
| 6,372,333 B1 | 4/2002 | Sugiyama et al. | |
| 6,410,618 B2 | 6/2002 | Uryu et al. | |
| 6,534,084 B1 | 3/2003 | Vyakarnam et al. | |
| 2002/0114795 A1 | 8/2002 | Thorne et al. | |
| 2003/0065400 A1 | 4/2003 | Beam et al. | |
| 2005/0240281 A1 | 10/2005 | Slivka et al. | |

OTHER PUBLICATIONS

Serafica, et al., "Inclusion of Solid Particles in Bacterial Cellulose" Appln. Microbiol. Biotechnol. (2002) pp. 756-760, vol. 58.
Grimandi, et al., "In Vitro Evaluation of a New Injectable Calcium Phosphate Material" J. Biomed. Mater. Res. (1998) pp. 660-666, vol. 39.
Yamanaka, et al., "The Structure and Mechanical Properties of Sheets Prepared from Bacterial Cellulose" Journal of Materials Science (1989) pp. 3141-3145.
Yamada, et al., "The Phylogency of Acetic Acid Bacteria Based on the Partial Sequences of 16S Ribosomal RNA: The Elevation of the Subgenus Gluconoacetobacier to the Generic Level" Biosci. Biotech. Biochem (1997) pp. 1244-1251, vol. 61, No. 8.
Märtson, et al., "Biocompatibility of Cellulose Sponge with Bone" Eur. Surg. Res. (1998) pp. 426-432, vol. 30.
"Bone Graft Substitutes Safe, Effective" American Medical Association Science News (Dec. 6, 2001) pp. 1-2.
Novaes, Jr. et al., "Gengiflex, an Alkali-Cellulose Membrane for GTR: Histologic Observations" Braz. Dent J. (1993) pp. 65-71, vol. 4, No. 2.
Gutowska, et al., "Injectable Geks for Tissue Engineering" The Anatomical Record (2001) pp. 342-349, vol. 263.
Bensen, et al., "Preclinical Evaluation of Bone Graft Substitutes" Biomaterials and Bioengineering Handbook (2000) pp. 699-715, vol. 31.
Burg, et al., "Biomaterial Developments for bone Tissue Engineering" Biomaterials (2000) pp. 2347-2359, vol. 21.
Ducheyne, et al., "Bioactive Ceramics: The Effect of Surface Reactivity on Bone Formation and Bon Cell Function" Biomaterials (1999) pp. 2287-2303, vol. 20.
Fricain, et al., "Cellulose Phosphates as Biomaterials. In vivo Biocompatibility Studies" Biomaterials (2002) pp. 971-980, vol. 23.
Fontana, et al., "Acetobacter Cellulose Pellicle as a Temporary Skin Substitute" Applied Biochemistry and Biotechnology (1990) pp. 253-264, vol. 24/25.
Gresser, et al., "Engineering of Resorbable Grafts for Craniofacial Reconstruction" Biomaterials and Bioengineering Handbook (2000) pp. 675-697, vol. 30.
Iguchi, et al., "Bacterial Cellulose—A Masterpiece of Nature's Arts" J. Materials Science (2000) pp. 261-270, vol. 35, No. 2.
Klemm, et al., "Bacterial Synthesized Cellulose—Artificial Blood Vessels for Microsurgery" Prog. Polym. Sci (2001) pp. 1561-1603, vol. 26.
Märtson, et al., "Is Cellulose Sponge Degradable or Stable as Implantation Material? An in vivo Subcutaneous Study in the Rat" Biomaterials (1999) pp. 1989-1995, vol. 20.
Mello, et al., "Duraplasty with Biosynthetic Cellulose: An Experimental Study" J. Neurosurg. (1997) pp. 143-150, vol. 86.
Miyamoto, et al., "Tissue Biocompatibility of Celluslose and its Derivatives" J. of Biomedical Materials Research (1989) pp. 125-133, vol. 23.
Mortier, et al., "Synthesis and Thermal Behavior of Well-Crystallized Calcium-Deficient Phosphate Apatite" Journal of Solid State Chemistry (1989) pp. 215-219, vol. 78.

(Continued)

*Primary Examiner* — Susan Tran

(74) *Attorney, Agent, or Firm* — Scully, Scott, Murphy & Presser, P.C.

(57) ABSTRACT

A composite biocompatible hydrogel material includes a porous polymer matrix, the polymer matrix including a plurality of pores and providing a Young's modulus of at least 10 GPa. A calcium comprising salt is disposed in at least some of the pores. The porous polymer matrix can comprise cellulose, including bacterial cellulose. The composite can be used as a bone graft material. A method of tissue repair within the body of animals includes the steps of providing a composite biocompatible hydrogel material including a porous polymer matrix, the polymer matrix including a plurality of pores and providing a Young's modulus of at least 10 GPa, and inserting the hydrogel material into cartilage or bone tissue of an animal, wherein the hydrogel material supports cell colonization in vitro for autologous cell seeding.

2 Claims, 3 Drawing Sheets

(56) References Cited

OTHER PUBLICATIONS

Schramm, et al., "Factors Affecting Production of Cellulose as the Air/Liquid Interface of a Culture of Acetobacter Xylinum" J. Gen. Microbiol. (1954) pp. 123-129, vol. 11.

Takaoka, et al., "Bone-Inducing Factors in Oxteoinductive Implants" Human Biomaterials Applications (1996) pp. 91-98, vol. 4.

Tas, A.C., "Synthesis of Biomimetic Ca-Hydroxyapatite Powders at 37•On Synthetic Body Fluids" Biomaterials (2000) pp. 1429-1438, vol. 21.

Varma, et al., "Porous Calcium Phosphate Coating Over Phosphorylated Chitosan Film by a Biomimetic Method" Biomaterials (1999) pp. 879-884, vol. 20.

Bourgeois, et al., "Calcium-deficient Apatite: A First in Vivo Study Concerning Bone Ingrowth" (2002) pp. 403-408.

METHOD OF TISSUE REPAIR USING A COMPOSITE MATERIAL

CROSS REFERENCE TO RELATED APPLICATION

This application is a divisional of U.S. patent application Ser. No. 10/295,461, filed Nov. 15, 2002 the entire content and disclosure of which is incorporated herein by reference.

STATEMENT REGARDING FEDERALLY SPONSORED RESEARCH

The United States Government has rights in this invention pursuant to Contract No. DE-AC05-00OR22725 between the United States Department of Energy and UT-Battelle, LLC.

FIELD OF THE INVENTION

The invention relates generally to the fields of biomaterials. More particularly, the invention relates to artificial bone compositions and methods of forming and using such compositions.

BACKGROUND

Bone grafting is a technique used to repair or help in the healing of osseous damage caused by procedures and pathologies such as surgery, tumors, trauma, congenital deformities, implant revisions, and joint fusions. The two most common methods presently used to restore bone are allografting and autografting.

Allografting, which comprises transplantation of tissue from a donor into a host subject, has both clinical and practical drawbacks. Clinically, allografting exposes the host subject to a risk of acquiring an infection and/or other disease such as a host immune system-mediated anti-graft response. Practical problems with this procedure are that donor tissue is often expensive or unavailable.

Autografting, which comprises the transplantation of autologous tissue from one site in a subject's body to another, suffers fewer problems as compared to allografting. For example, because the host and donor are the same subject, the risk of infection and immune system-mediated rejection are significantly reduced. However, autografting is still disadvantageous in that it requires that two separate surgical procedures (one to harvest the tissue; one to transplant the tissue) to be performed on the subject. Additionally, the supply of usable autologous bone is limited because it is collected from only one subject.

To avoid problems associated with allografting and autografting, synthetic bone-grafting materials have been developed. Synthetic bone-grafting materials offer numerous clinical and practical advantages. The clinical advantages include (1) reduced risk of infection and/or rejection and (2) no complications from tissue harvesting surgery. Practical advantages of using synthetic materials include the possible selection of materials that exhibit superior mechanical properties, materials which can be fashioned into custom-made shapes and sizes, and materials which can be made in large quantities.

A number of different compositions have been used as synthetic materials for bone grafting. Predominant among these are calcium phosphates such as hydroxyapatite. Hydroxyapatite, the main mineral component in bone, is the most stable calcium phosphate form under normal physiological conditions. It is a particularly good material for use in bone grafting because it readily bonds with bone, and is biocompatible and osteoinductive, permitting bone repair in a location that would not normally heal if left untreated. Used alone, however, hydroxyapatite lacks mechanical strength and cannot withstand substantial stress.

SUMMARY

A composite biocompatible hydrogel material includes a porous polymer matrix, the polymer matrix including a plurality of pores and providing a Young's modulus of at least 10 GPa. The porous polymer matrix can comprise cellulose or cellulose derivatives, including bacterial cellulose. A calcium comprising salt is disposed in at least some of the pores.

The calcium salt can include calcium phosphate. Calcium phosphate is preferably in the form of hydroxyapatite, hydroxyapatite being the most stable form of calcium phosphate and the main mineral component found in bone. The calcium salt may include carbonate or fluoride.

A synthetic hone graft material includes a porous polymer matrix, the polymer matrix including a plurality of pores and providing a Young's modulus of at least 10 GPa. A calcium salt is disposed in at least some of the pores. The polymer can include cellulose or cellulose derivatives, such as bacterial cellulose. The calcium salt can include calcium phosphate in the form of hydroxyapatite. The calcium salt may include carbonate or fluoride. The bone graft material can also include bone morphogenetic proteins (BMP's) or chondrocytes which can be disposed in at least some of the plurality of pores.

A method of tissue repair within the body of animals includes providing a composite biocompatible hydrogel material including a porous polymer matrix, the polymer matrix including a plurality of pores and providing a Young's modulus of at least 10 GPa, and a calcium comprising salt disposed in at least some of the pores. The hydrogel material is inserted into cartilage or bone tissue of an animal, wherein the hydrogel material supports cell colonization in vitro for autologous cell seeding.

A method of forming a biocompatible composite hydrogel material includes the steps of providing a porous polymer matrix, the polymer matrix including a plurality of pores and providing a Young's modulus of at least 10 GPa, and impregnating the pores with a calcium salt. The impregnating step can include the steps of immersing the polymer matrix into a solution containing a calcium source and immersing the polymer matrix in a solution including a source of phosphate, wherein calcium phosphate is formed in the pores. Alternatively, the impregnating step can include the steps of phosphorylating the polymer and immersing the phosphorylated polymer in a calcium including solution.

The polymer matrix is preferably generated by bacteria from the genus *Gluconacetobacter*, whereby the polymer formed includes cellulose or cellulose derivatives. The bacteria can be *Gluconacetobacter hansenii*. The calcium salt can be calcium phosphate, calcium fluoride or calcium carbonate. Calcium phosphate is preferably in the form of hydroxyapatite.

BRIEF DESCRIPTION OF THE DRAWINGS

The invention is pointed out with particularity in the appended claims. The above and further advantages of this invention may be better understood by referring to the following description taken in conjunction with the accompanying drawings, in which:

DETAILED DESCRIPTION

Figure 1:
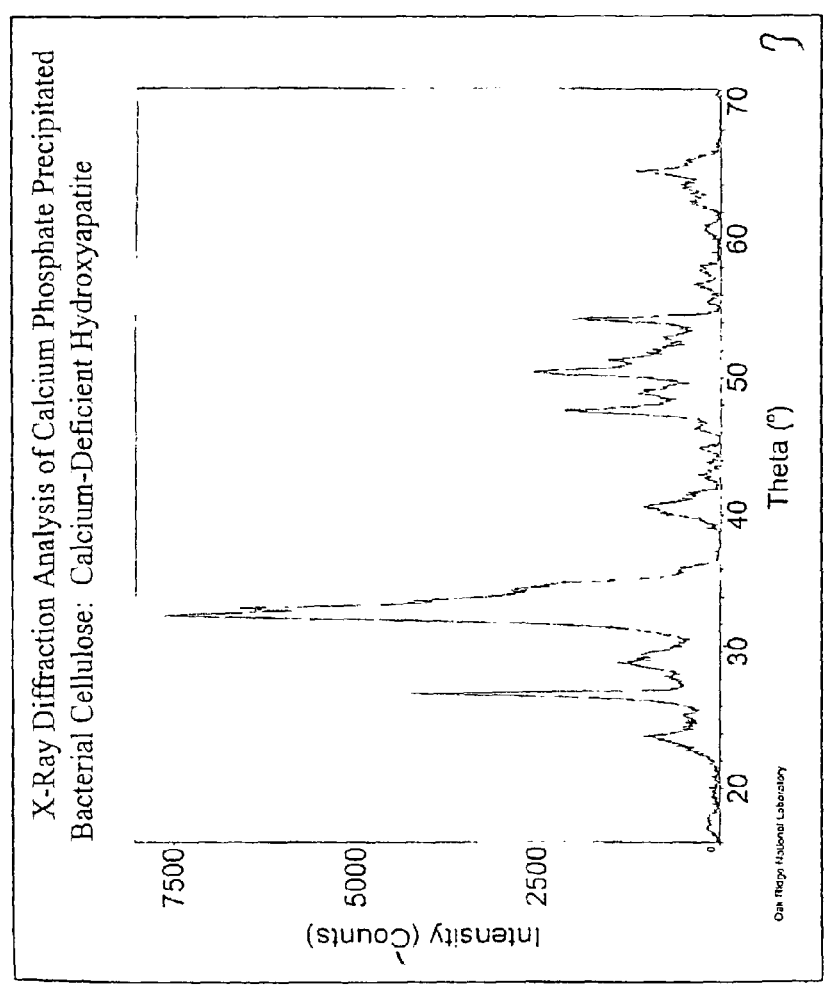
FIG. 1 is an X-Ray Diffraction (XRD) pattern of calcium phosphate precipitated in bacterial cellulose.

A composite biocompatible hydrogel material includes a porous polymer matrix, the polymer matrix including a plurality of pores and providing a Young's modulus of at least 10 GPa, preferably at least 20 GPa, and more preferably at least 24 GPa. A calcium comprising salt can be disposed in some of the pores of the polymer. As used herein, the term "hydrogel" refers to a three dimensional networks of hydrophilic polymers that are insoluble. Since the Young's modulus of human bone generally ranges from 12 to 24 GPa, the polymer matrix and resulting composite material is strong enough to withstand the stress and strain necessary for use as a practical orthopedic biomaterial, even in load bearing applications.

The porosity of the bacterial cellulose polymer enables it to be very well suited for use as a template for formation of a hydroxyapatite composite for bone tissue regeneration. Bacterial cellulose contains 99.3% water in its hydrated natural form allowing infusion of both large and small molecules into its matrix.

The calcium salt can comprise calcium fluoride, calcium carbonate or calcium phosphate. Calcium phosphate is preferably in the form of hydroxyapatite, hydroxyapatite being the most stable form of calcium phosphate and the main mineral component of bone. If the composite is used in dental applications, some concentration of fluorine is preferably included, such as from a calcium salt or calcium fluoride, due to the known cavity preventing properties of fluoride.

Cellulose formed by bacteria is referred to as bacterial cellulose or biocellulose. This is the preferred form of cellulose for formation of the composite material. The Young's modulus of bacterial cellulose has been reported to be 16-18 GPa, and can be improved up to 30 GPa by further purification (Yamanaka et al. J. Mat. Sci. 24: 3141-3145 1989).

Bacterial cellulose offers significant advantages over plant cellulose since it is inherently nearly pure, is highly crystalline, and contains greater than 99% water. In addition, it forms an intricate highly interconnected network of fibers with dimensions of approximately 5×0.1×0.004 µm. In contrast, cylindrical cotton fibers are about 70 µm (diam.) and are arranged in parallel bundles. Bacterial cellulose can be obtained commercially from food production companies in Southeast Asia or synthesized by organisms such as bacteria.

Synthesis by bacteria is known to permit control of the physical properties of the cellulose product formed, such as molecular weight and crystallinity. It may also be possible to directly synthesize cellulose derivatives using bacteria, such as cellulose that contains amine groups (Yamada et al. Biosci. Biotechnol. Biochem. 61: 8 1244-1251 1997).

The preferred species of bacterial for this application are the gram negative acetic acid bacteria of the genus *Acetobacter*, reclassified in 1997 by Yamada et al. to *Gluconoacetobacter, xylinus* and *Gluconoacteobacter hansenii* (synonyms *Gluconacetobacter xylinus* and *Gluconacetobacter hansenii*).

*G. xylinus* and *G. hansenii* are known to produce a gel-like, hydrated form of cellulose with a highly porous structure. This bacterial cellulose includes a plurality of fibers, the fibers having an average diameter of about 100 nm.

The composite may be formed by a two step process, described below for formation of a bacterial cellulose calcium phosphate composite. First, samples of bacterial cellulose are permeated by a solution of soluble calcium salt, such as $CaCl_2$. Other calcium solutions can be used, such as calcium hydroxide, calcium nitrate, and simulated body fluid.

In a second step, the sample is then soaked in a phosphate salt to precipitate calcium phosphate in the polymer matrix. Sodium phosphate dibasic is preferred for this purpose. Alternative phosphate solutions for the precipitation of calcium phosphate into bacterial cellulose include potassium phosphate dibasic, sodium tripolyphosphate, and diammonium phosphate. In addition, the order of infusion of the salts can be reversed. This process produces a flexible and durable hydrogel composite comprising calcium phosphate crystals deposited within the porous bacterial cellulose matrix. X-ray diffraction studies performed have confirmed that the calcium phosphate deposited is in the form of hydroxyapatite, the main mineral component of bone (See FIG. 1). The peak at 22 theta corresponds to crystalline cellulose and the other peaks are characteristics of calcium deficient hydroxyapatite (Pattern Diffraction Database, Mortier et al. J. Solid State Chem. 78: 215 1989).

Optionally, fluoride salts (e.g. from aqueous KF) can be used to fluoridate the hydroxyapatite precipitated in the bacterial cellulose in a separate step. Fluoride is a natural trace element in hydroxyapatite and is useful in dental applications to prevent cavities. Carbonate salts (e.g. from aqueous $Na_2CO_3$) can be used to add carbonate ions onto hydroxyapatite precipitated in the bacterial cellulose to more closely resemble biological apatite. This may accelerate replacement with bone since carbonate-apatite can be dissolved significantly faster as compared to carbonate-free-apatite.

In an alternate method, phosphate groups can be chemically attached to bacterial cellulose using a phosphorylation process. Precipitation occurs when the phosphorylated cellulose is incubated in calcium containing salt solutions. This process can improve the mechanical properties of the composite and its ability to retain its shape. Calcium solutions, such as simulated body fluid, aqueous calcium chloride, aqueous calcium hydroxide, or a combination of the theses solutions can be used for this purpose.

Unlike pure hydroxyapatite, the composite hydrogel material is neither stiff nor brittle. It does, however, retain the advantageous property of hydroxyapatite for bone grafting applications, that being bondable to bone, biocompatible, and osteoinductive. The invention can also be used for a wide variety of other biomaterial applications, such as dental grafts, ocular implants, or artificial cartilage.

Used as a bone grafting material, bacterial cellulose can be used as a carrier for bone morphogenetic proteins (BMP's). BMP's initiate bone formation and regulate cartilage and bone differentiation in the body. BMP's could be seeded into porous polymers such as native bacterial cellulose or calcium phosphate impregnated bacterial cellulose.

Implanting of chondrocytes into the bacterial cellulose matrix can be used to aid in cartilage reconstruction. Chondrocytes can be seeded into porous polymers such as native bacterial cellulose or calcium phosphate impregnated bacterial cellulose.

The composite material is quite suitable for use as a bone implant or repair material for numerous reasons. First, it is stable when in contact with body fluid and other aqueous solutions. Second, polymers such as cellulose have low toxicity and are biocompatible. Third, the porous nature of the polymer selected (e.g. bacterial cellulose) allows the composite to support bone ingrowth. Moreover, when bacterially produced polymers are used, the polymers can be made into any shape or size by growing the bacterial polymers (e.g.) cellulose in appropriate molds, or sizing the material by cutting.

Other applications for the composite will be apparent to those skilled in the art. For example, the composite hydrogel can also be used for absorption of materials. Hydroxyapatite immobilized in bacterial cellulose can be used for absorption of proteins. The composite can also provide a hydroxyapatite source for binding water or soil contaminants such as Pb, Cd, Zn, U, and Sr or for removal of metal ions from aqueous solution.

EXAMPLES

The present invention is further illustrated by the following specific examples. The examples are provided for illustration only and are not to be construed as limiting the scope or content of the invention in any way.

Example 1

Deposition of Calcium Phosphate in Bacterial Cellulose

Cubes (1 cm$^3$) of bacterial cellulose obtained from the commercial food product Nata de Coco REM Corporation, Pioneer cor. Sheridan, Mandaluyong, Metro Manila, Philippines were extensively soaked in HPLC-grade distilled water to remove sucrose added during calming. The cellulose was further cleaned by soaking in 1 M sodium hydroxide, followed by neutralization with acetic acid and soaking in distilled water to remove salts. The cubes were stored in 20% ethanol. Twelve cellulose cubes were soaked in 50 mM calcium chloride ($CaCl_2$) (pH 4.83) for 18 hours. A first set of three cubes was then placed in distilled water as a control. A second set of three cubes was rinsed with distilled water, then soaked in 100 mM sodium phosphate dibasic ($Na_2HPO_4$) (pH 9.30). A third set of three cubes was soaked in 100 mM sodium bicarbonate (pH 8.36). And a fourth set of three cubes was soaked in 100 mM sodium carbonate (pH 11.8) for 18 h. All incubations were carried out at 23° C. After 18 h, the cubes were removed from the solutions, rinsed with nanopure water, dried, and examined under the microscope at 1× and at 100× magnification. The bicarbonate and carbonate samples were observed to contain crystal-like structures deposited on the surface of the cellulose. The phosphate sample was covered with a smooth coating which was rigid and was about three-fold thicker than the control after drying.

In a further experiment, a sample of bacterial cellulose was produced under controlled laboratory conditions with the strain ATCC 10821 *Gluconoacetobacter hansenii* (obtained from the American Type Culture Collection, Manassas, Va.). A round pellicule of 9 cm diameter and 5 mm thick produced by growth of the bacteria in 150 ml of Schramm-Hestrin medium (see Example 2) was cleaned with hot water and sodium hydroxide, followed by neutralization with acetic acid, soaking in water, and storage in 20% ethanol. This pellicule was cut into fourths, and two of the four pieces were incubated with 50 mM calcium chloride for 18 h at 23° C. with agitation. The calcium solution was decanted and the cellulose pieces were washed with nanopure water. Then 80 ml of sodium phosphate dibasic, pH 9.3, were added to the cellulose.

After 3 h incubation, the phosphate was decanted and fresh phosphate solution was added to the cellulose pieces. After another 4 h, the phosphate was decanted, the pieces were washed with nanopure water, and then the pieces were soaked in 80 ml of calcium chloride for 18 h. The calcium solution was then decanted, and the two pieces were again soaked in two 4-h changes of phosphate. Finally, the phosphate was decanted, and the pieces of cellulose were rinsed in nanopure water. One piece of the calcium and phosphate cellulose and one piece of untreated control cellulose were dried on a gel drier and then air-dried. The other pieces were stored in 20% ethanol to prevent microbial growth. The appearance and physical properties of the slices of cellulose pellicule treated with calcium and phosphate resembled those of the commercial Nata de coco that had been treated with these two salts.

Example 2

Production of Bacterial Cellulose and Modulation of its Properties

For synthesis of cellulose layers (pellicules), a seed culture of *G. hansenii* was grown in Schramm-Hestrin medium (Schramm and Hestrin, J. Gen. Microbiol. 11:123, 1954) in a flask under agitated conditions. This seed culture is diluted 1/10 with Schramm-Hestrin medium and transferred to sterile containers for static growth. The cellulose is formed at the air-liquid interface. Clouds of cellulose begin to form in the medium within 1-2 days at 23° C. The cellulose pellicules can be harvested after 5-8 days depending on the thickness desired. The fastest synthesis of cellulose is seen with glucose as the supplied sugar. Cellulose is synthesized more slowly when the bacteria are grown on medium containing cellobiose, mannitol, or fructose. A synthetic medium (Cannon and Anderson, Crit. Reviews in Microbiol. 17:435, 1991) can be used instead of the Schramm-Hestrin medium, but cellulose formation is slower than in the rich medium.

After removal from the surface of the culture dish, the cellulose pellicules were first heated to 90° C. in HPLC-grade distilled water for 1-2 h. The pellicules were rinsed with water, then treated with 1% sodium hydroxide for 1-7 days at 23° C. The sodium hydroxide was neutralized by addition of 1.2 volumes of 500 mM sodium acetate buffer, pH 4.5, followed by soaking in distilled water. The washed pellicules were then stored in 20% ethanol. The surface area and shape of the pellicule is determined by the size and shape of the static cultivation container. As the bacteria are aerobic, cellulose production is enhanced when the cultures are performed in shallow containers with a total liquid depth of not more than 5 cm. Containers successfully used included 60- and 100-mm diameter disposable culture dishes, 10 ml glass beakers, 20×20 cm glass baking dishes, and 2-liter flasks. Growth of larger pellicules is possible, as shown by the production of cellulose for Nata de Coco in flat pans of 1×1 m. Utilization of porous containers such as polyvinyl chloride gloves for cultivation is known to allow production of bacterial cellulose in versatile shapes and sizes.

The physical appearance of the bacterial cellulose was observed to vary dependent on the sugar used in the growth medium, the other nutrients added to the growth medium, and the agitation of the culture container during growth (stationary vs. shaker). When *G. hansenii* was grown in the rich Schramm-Hestrin medium under stationary conditions, a pellicule of cellulose formed at the air-liquid interface when both glucose and mannitol as the nutrient sugar. When such cultures were incubated in conical flasks on a shaker at low rotational speed, the glucose culture formed loose clumps, while the mannitol culture form dense, small pellets and balls. A synthetic medium offers the advantages of lower cost, fewer impurities in the product, and better incorporation of glucose analogs. Pellicules of bacterial cellulose grown in the rich Schramm-Hestrin medium grew fastest and appeared white and dense. These pellicules dried to white or translucent membranes about 30-60 microns thick. Those grown in the synthetic medium grew more slowly and had a gel-like, translucent appearance, drying to transparent, very thin, sticky membranes. The pellicules from synthetic medium appear to be more porous.

Example 3

Identification of Calcium Phosphate

The incorporation of calcium and phosphate in the bacterial cellulose was quantified using Laser Induced Breakdown Spectroscopy (LIBS) and X-Ray Diffraction (XRD). In LIBS, a laser transforms the material into a plasma spark. The spectral emissions from this spark can be evaluated by a spectrometer to determine the material's elemental breakdown. When an x-ray is directed at a particular substance in the XRD procedure, it will diffract the x-ray at a specific angle. The unique diffraction pattern can thus be used to identify the material.

Proof of calcium and phosphate induction into the matrix was first confirmed using LIBS. The laser used was a Spectra Physics pulsed Nd:YAG laser (Model INDI-SHG-50) with a fundamental wavelength of 1064 nm. The frequency was doubled to give an output wavelength of 532 nm, and the frequency was quadrupled to give a 266 nm wavelength. The spectrometer was a 0.5 m Acton spectrometer (Model SP 500) which had a resolution of 0.05 nm. The procedure was executed on one sample of bacterial cellulose derived from *Gluconacetobacter hansenii* in Schramm-Hestrin Media, rinsed in hot water and 2% SDS. The sample was incubated in 200 mL of 50 mM $CaCl_2$ for 18 hours. It was then rinsed in nanopure water, and soaked in 200 mL of 50 mM $Na_2HPO_4$ for 4 hours. The sample was decanted, added to a fresh 200 mL of 50 mM $Na_2HPO_4$, and incubated for another 4 hours. After rinsing in nanopure water, it was again submerged in 200 mL of 50 mM $CaCl_2$ for 18 hours. It was then rinsed in nanopure water, and soaked in 200 mL of 50 mM $Na_2HPO_4$ for 4 hours. The sample was decanted, added to a fresh 200 mL of 50 mM $Na_2HPO_4$, and incubated for another 4 hours. All incubations were carried out at 23° C. After a final rinse in nanopure water, the sample was put on a gel-dryer for 30 minutes.

Figure 2:
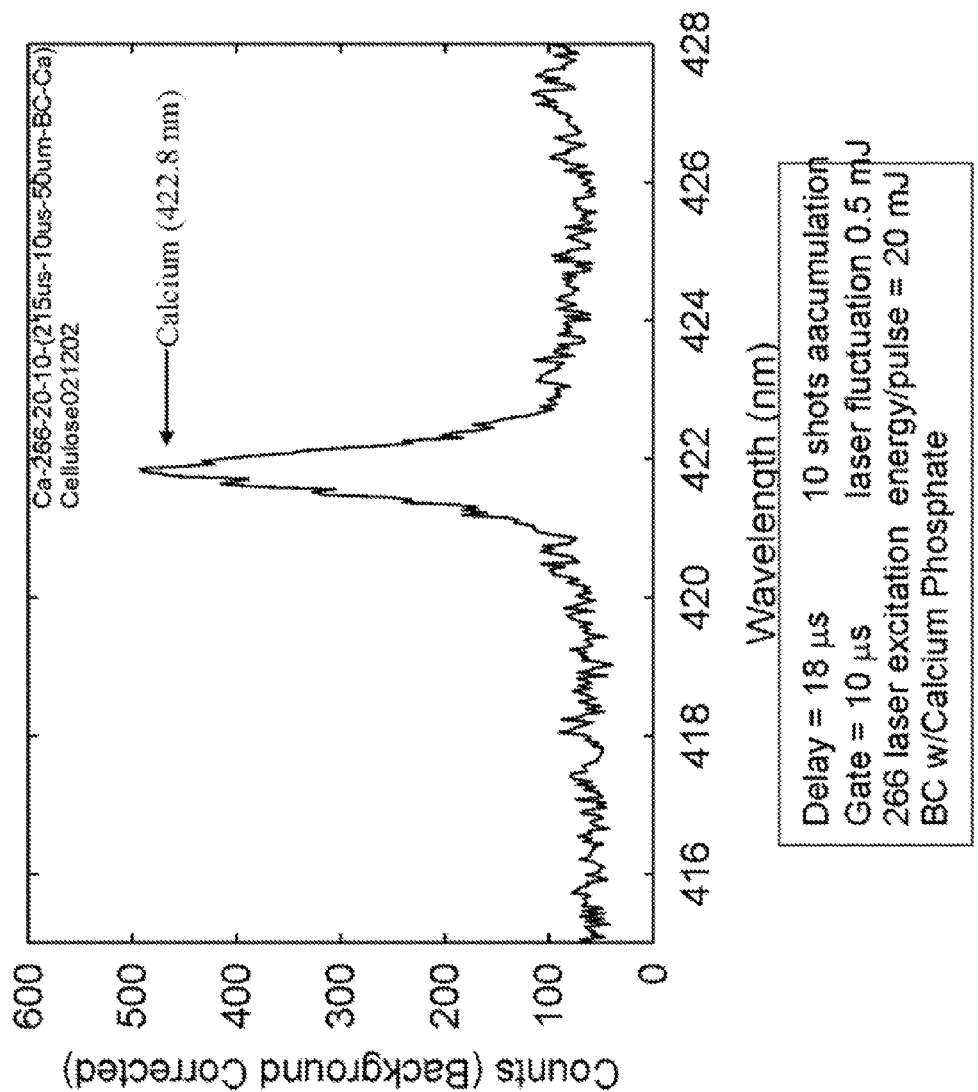
FIG. 2 shows a Laser Induced Breakdown Spectroscopy (LIBS) signal for calcium in bacterial cellulose loaded with calcium phosphate.
Figure 3:
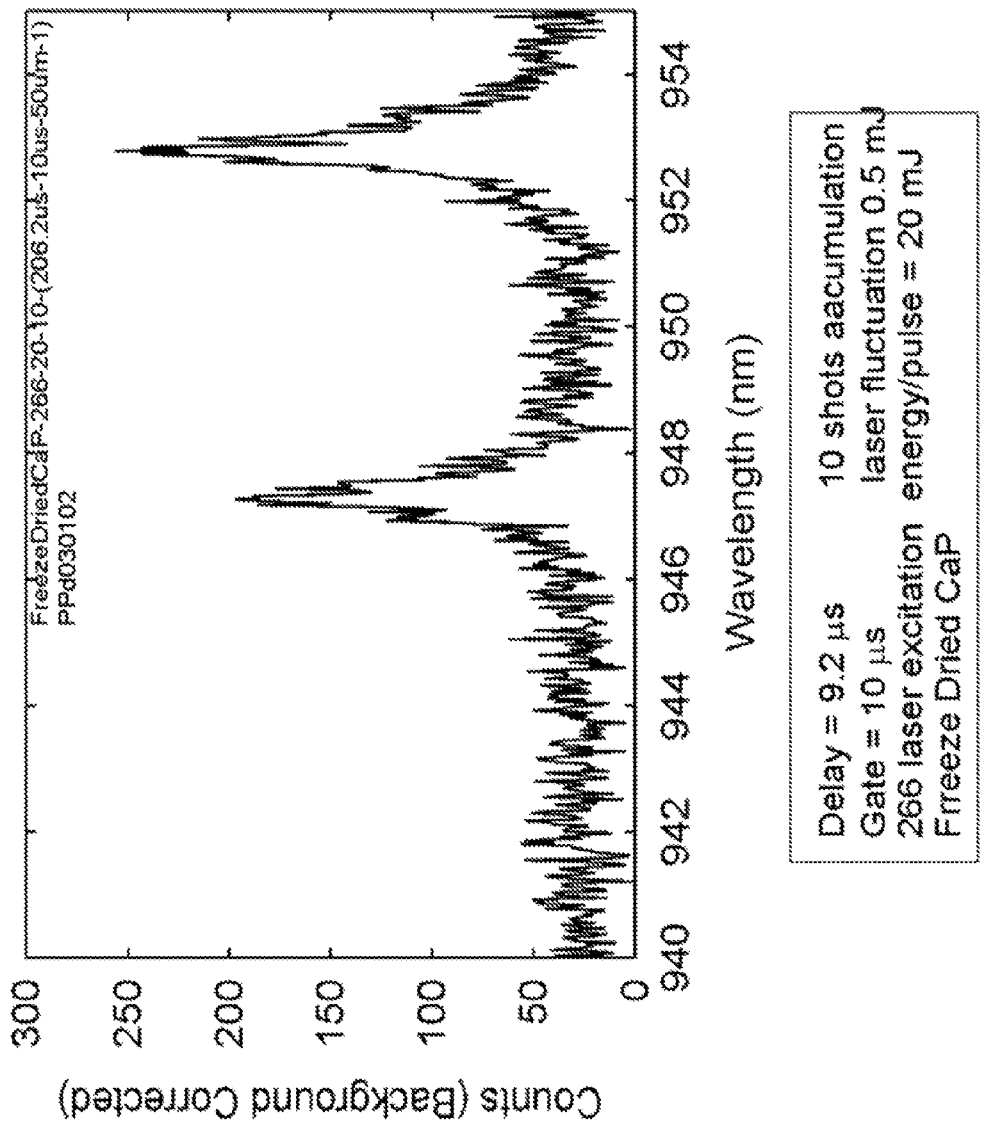
FIG. 3 shows a Laser Induced Breakdown Spectroscopy (LIBS) signal for phosphorous in bacterial cellulose loaded with calcium phosphate.

FIGS. 2 and 3 show LIBS signals for calcium and phosphorous, respectively, in bacterial cellulose loaded with calcium phosphate. The peak at 422.8 nm in FIG. 2 indicates the presence of calcium. The peaks at 949 nm and 952.8 nm in FIG. 3 indicate the presence of phosphorus.

An x-ray diffraction analysis of calcium phosphatye precipitated in bacterial cellulose is shown in FIG. 1 As noted earlier, the peak at 22 theta corresponds to crystalline cellulose and the other peaks shown are characteristics of calcium deficient hydroxyapatite ($Ca_9HPO_4(PO_4)_5OH$). The measurements were made with a Siemens D5005 X-Ray Diffraction Machine. The sample was run with a step-scanning mode of $2\theta=15.0$ and a count time of 20 s. The Cu K tube operated at 40 kV and 20 mA. The sample used was a 6-cm pellicule derived from *Gluconacetobacter hansenii* grown in Schramm-Hestrin media. The cellulose was purified using hot water and 0.5% NaOH, and 1% SDS. The sample was incubated in 150 mL of 100 mM $CaCl_2$ for 1 day. It was then rinsed with nanopure water, and incubated in 150 mL of 60 mM $Na_2HPO_4$ for 1 day. This cycle was repeated two more times for a total of 3 daily soakings of 100 mM $CaCl_2$ alternated with 3 daily soakings of 60 mM $Na_2HPO_4$ carried out at 23° C. It had a final rinse in nanopure water before being put on a gel-dryer for 30 minutes. The x-ray diffraction pattern matches that of calcium-deficient hydroxyapatite ($Ca_9HPO_4(PO_4)_5OH$) as discovered by Mortier et al. (J. of Solid State Chem. 78:215, 1989).

Example 4

Behavior of Bacterial Cellulose in Simulated Body Fluid

When the bacterial cellulose was submerged in simulated body fluid, a biomimetic apatite formed in its matrix. Apatite is identified as a natural, variously colored calcium fluoride phosphate, $Ca_5F(PO_4)_3$, with chlorine, hydroxyl, or carbonate sometimes replacing the fluoride. When calcium phosphate bacterial cellulose was incubated in simulated body fluid, its apatite content increased even more significantly. This behavior indicated that bacterial cellulose will act favorably as an orthopedic implant. Instead of being encapsulated by fibrous tissue, the apatite layer induced by the physiological environment material should bond directly with bone. Drying and weighing the precipitated samples in comparison to an unaltered sample of bacterial cellulose confirmed the presence of additional apatite formed when the bacterial cellulose was exposed to the simulated body fluid. The use of alizarin red S, a dye commonly used to identify calcium in histology, also indicated that calcium was incorporated into the matrix.

Simulated body fluid was prepared from a protocol developed by Tas (Biomaterials 21: 1429-1438 2001). The ion concentrations of the simulated body fluid mimic that of human plasma (Table 1).

TABLE 1

Ion Concentrations of Simulated Body Fluid compared to Human Plasma

| Ion | Human Plasma | Simulated Body Fluid |
|---|---|---|
| $Na^+$ | 142.0 mM | 142.0 mM |
| $Cl^-$ | 103.0 mM | 125 mM |
| $HCO_3^-$ | 27.0 mM | 27.0 mM |
| $K^+$ | 5.0 mM | 5.0 mM |
| $Mg^{2+}$ | 1.5 mM | 1.5 mM |
| $Ca^{2+}$ | 2.5 mM | 2.5 mM |
| $HPO_4^{2-}$ | 1.0 mM | 1.0 mM |
| $SO_4^{2-}$ | 0.5 mM | 0.5 mM |

TABLE 2

Chemical Composition of Simulated Body Fluid Solution

| Reagent | SBF (g/L) |
|---|---|
| NaCl | 6.547 |
| $NaHCO_3$ | 2.268 |
| KCl | 0.373 |
| $Na_2HPO_4 \cdot 2H_2O$ | 0.178 |
| $MgCl_2 \cdot 6H_2O$ | 0.305 |
| $CaCl_2 \cdot 2H_2O$ | 0.368 |

The reagents in Table 2 are combined and titrated to pH 7.40 at 37° C. 8 6-cm bacterial cellulose pellicules were made in an identical fashion from the *Gluconacetobacter hansenii* strain grown in Schramm-Hestrin media. The samples were cleaned with hot water and 1% sodium dodecyl sulfate/1% sodium hydroxide solution. Two samples were reserved in water as a control. Four samples were incubated in 200 mL of 100 mM $CaCl_2$ for one day, followed by incubation in 200 mL of 60 mM $Na_2HPO_4$ for one day, with 2 more cycles in the same fashion carried out at 23° C. Two of the calcium phosphate pellicles were incubated in 100 mL of simulated body fluid for 11 days at 23° C. The fluid was changed 5 times throughout the duration. Two unaltered samples of cellulose were also incubated in simulated body fluid for 11 days at 23° C., with the solution being changed 5 times throughout the duration. The four sets of cellulose samples were completed as follows: 2 pellicles of unaltered bacterial cellulose, 2 pellicules of bacterial cellulose incubated in simulated body fluid, 2 pellicles of calcium-phosphate bacterial cellulose, and 2 pellicles of calcium-phosphate bacterial cellulose incubated in simulated body fluid.

One pellicule from each pair was dried on the gel-dryer for 30 minutes and weighed (Table 3).

TABLE 3

Weights of Bacterial Cellulose and Calcium Phosphate Bacterial Cellulose in Simulated Body Fluid

| Sample | Dry Weight |
|---|---|
| Unaltered Bacterial Cellulose | 0.0428 g |
| Bacterial Cellulose Incubated in Simulated Body Fluid | 0.0540 g |
| Calcium Phosphate Bacterial Cellulose | 0.1858 g |
| Calcium Phosphate Bacterial Cellulose Incubated in Simulated Body Fluid | 0.2435 g |

The other pellicules were each stained in 10 mL of 2% Alizarin Red S. The dyed samples were subsequently rinsed in nanopure water and put on the gel-dryer for 30 minutes. The increase in weight and visual observation with and without staining indicates apatite formation after submersion in simulated body fluid.

Example 5

Modifying Apatite Formation within the Matrix

The amount of calcium phosphate incorporated into the bacterial cellulose can be altered in at least two ways: (1) varying the number of soaking cycles of the calcium chloride and sodium phosphate dibasic solutions, or (2) by changing the molarity of the calcium chloride and sodium phosphate dibasic solutions.

Varying the Number of Incubation Cycles. Four 10-cm bacterial cellulose pellicules were synthesized from cultures of *Gluconacetobacter hansenii* strain grown in Schramm-Hestrin media as described above. The pellicules were cleaned with hot water and 2% sodium dodecyl sulfate. One pellicule was stored in water as a control. A second pellicule was incubated in 150 mL of 50 mM $CaCl_2$ for 18 hours, and then rinsed in nanopure water. The cellulose was then incubated in 150 mL of 100 mM $Na_2HPO_4$ for 4 hours, decanted, and then added to another 150 mL of 100 mM $Na_2HPO_4$ for another 4 hours. The cellulose was rinsed, and again suspended in 150 mL of 50 mM $CaCl_2$ for 18 hours, then rinsed in nanopure water. The cellulose was again incubated in 150 mL of 100 mM $Na_2HPO_4$ for 4 hours, decanted, and then added to another 150 mL of 100 mM $Na_2HPO_4$ for another 4 hours. The pellicule went through another soaking in $CaCl_2$ and $Na_2HPO_4$ for a total of 3 cycles of incubation. The third pellicule underwent 4 cycles of $CaCl_2$ incubation followed by $Na_2HPO_4$ incubation. The last pellicule undertook 5 cycles of $CaCl_2$ incubation followed by a $Na_2HPO_4$ incubation. All incubations were carried out at 23° C. The 4 pellicules were weighed in their hydrated state. The samples were then put on a gel-dryer for 30 minutes, and baked in a 90° C. oven until a constant weight was reached (Table 4).

TABLE 4

Weights of Bacterial Cellulose Precipitated in Varying Number of Solution Cycles

| Sample | Wet Weight | Dry Weight |
|---|---|---|
| Unaltered Bacterial Cellulose | 1.00 g | 0.0690 g |
| Bacterial Cellulose Incubated in 3 cycles of 50 mM $CaCl_2$ and Sodium Phosphate Dibasic Solutions | 2.73 g | 0.3186 g |
| Bacterial Cellulose Incubated in 4 cycles of Calcium Chloride and Sodium Phosphate Dibasic Solutions | 3.40 g | 0.5940 g |
| Bacterial Cellulose Incubated in 5 cycles of Calcium Chloride and Sodium Phosphate Dibasic Solutions | 4.55 g | 0.6798 g |

The above results show an incremental weight gain with the increasing number of cycles of incubation in the 2 solutions. This indicates that the amount of calcium phosphate grows with the number of solution cycles.

The effect of varying the molarity of the immersion solutions was investigated. Ten 9-cm bacterial cellulose pellicules were synthesized from cultures of *Gluconacetobacter hansenii* strain grown in Schramm-Hestrin media as described above. The samples were cleaned with hot water and 2% sodium dodecyl sulfate. Two of the pellicules were stored in water as controls. Each of the 8 pellicules were incubated in a particular molarity of $CaCl_2$ solution for 1 day, followed by incubation in a particular molarity of $Na_2PO_4$ for 1 day, then incubated again for 1 day in the aqueous $CaCl_2$, and again in a last soaking of the aqueous $Na_2PO_4$ for 1 day. All suspensions were carried out at 23° C. The molarity ratio of Ca to P was kept to 10:6 in each sample to mimic the Ca:P concentration of hydroxyapatite. The concentrations of calcium chloride ranged from 25 mM to 200 mM, and the sodium phosphate dibasic concentrations varied from 15 mM to 120 mM (Table 5).

TABLE 5

Weights of Bacterial Cellulose Incubated in Varying Concentrations Of Calcium Chloride and Sodium Phosphate Dibasic

| Sample | Molarity of $CaCl_2$ used in Incubation | Molarity of $Na_2HPO_4$ Used in Incubation | Wet Weight | Dry Weight |
|---|---|---|---|---|
| 1 | 200 mM | 120 mM | 12.49 g | 0.7865 g |
| 2 | 175 mM | 105 mM | 11.40 g | 0.6682 g |
| 3 | 150 mM | 90 mM | 11.13 g | 0.6015 g |
| 4 | 125 mM | 75 mM | 8.70 g | 0.5065 g |
| 5 | 100 mM | 60 mM | 7.56 g | 0.2948 g |
| 6 | 75 mM | 45 mM | 6.91 g | 0.3104 g |
| 7 | 50 mM | 30 mM | 8.49 g | 0.3757 g |
| 8 | 25 mM | 15 mM | 8.12 g | 0.1940 g |
| 9 | No Incubation | No Incubation | 13.79 g | 0.1028 g |

Upon completion of the last cycle, the pellicules were rinsed in nanopure water and weighed. The samples were put on a gel-dryer for 30 minutes, and weighed again. Table 5 displays the wet and dry weights for each sample. Although the data was inconsistent with samples 6 and 7, it is evident that increasing molarity concentrations of the soaking solutions causes increased weight gain in the pellicules. This indicates the increased synthesis of calcium phosphate.

Example 6

Alternative Reagents

Salt solutions other than calcium chloride and sodium phosphate dibasic can be used to precipitate calcium phosphate into bacterial cellulose. For example, potassium phosphate dibasic and sodium tripolyphosphate can be employed as the phosphate donor. Concentrated calcium hydroxide can be used as a calcium donor.

Potassium phosphate dibasic was used as a phosphate donor in an experiment. 3-6 cm pellicules derived from *Gluconacetobacter hansenii* and Schramm-Hestrin media were cleaned in hot water, 1% SDS/0.5% NaOH solution. One pellicule was reserved as control. The second pellicule was suspended in 100 mL of 100 mM $CaCl_2$ for 1 day, and then added to 100 mL of 60 mM $K_2HPO_4$. Precipitation was immediately observed. The cellulose went through 2 more additional daily cycles of 100 mM $CaCl_2$ alternated with 2 daily cycles of 60 mM $K_2HPO_4$. The precipitated sample is significantly whiter, stiffer, and thicker than the control. A third pellicule was precipitated by the original protocol using 100 mM $CaCl_2$ and 60 mM $Na_2HPO_4$. It was immersed in 3 daily cycles of the calcium chloride alternated with 3 daily cycles of the sodium phosphate dibasic. All three samples were weighed in their hydrated state. Then they were put on a gel-dryer for 30 minutes and re-weighed (Table 6).

TABLE 6

Weight of Ca—P Precipitated Bacterial Cellulose Using Different $PO_4^-$ Donors

| Sample | Wet Weight | Dry Weight |
| --- | --- | --- |
| Bacterial Cellulose Immersed in $CaCl_{2\,(aq)}$ and $K_2HPO_{4\,(aq)}$ | 7.576 g | 0.3595 g |
| Bacterial Cellulose Immersed in $CaCl_{2\,(aq)}$ and $Na_2HPO_{4\,(aq)}$ | 7.678 g | 0.2996 |
| Unaltered Bacterial Cellulose | 8.937 g | 0.0400 g |

The similar results of potassium phosphate dibasic as compared to the sodium phosphate dibasic confirm that it can be used as alternative phosphate solution.

Sodium tripolyphosphate was used as a phosphate donor in an experiment. Sodium Tripolyphosphate ($Na_5P_3O_{10}$) (STPP) has a peculiar behavior in the precipitation of calcium phosphate in the cellulose matrix. It can either have the role of a phosphate donor, or as an apatite eliminator. STPP is a water softener which will substitute sodium ions for calcium ions. However, when the cellulose was soaked in calcium chloride, then added to STPP solution, and again soaked in $CaCl_2$; a heavy calcium phosphate precipitate formed. When a pellicule that has already incorporated calcium phosphate into its matrix was soaked in STPP, the sodium ions of the STPP substituted the calcium ions in the precipitate thereby removing almost all of the apatite.

Two 6-cm pellicules derived from a culture of *Gluconacetobacter hansenii* in Schramm-Hestrin media were cleaned in hot water, 1% SDS/0.5% NaOH solution. Each pellicule was soaked in 3 daily cycles of 100 mL of 100 mM $CaCl_2$ alternated with 3 daily cycles of 100 mL of 60 mM $Na_5P_3O_{10}$ for 1 day. One pellicule was removed after the last cycle of STPP. The other was soaked in an additional treatment of 100 mL of 100 mM $CaCl_2$ for one day. The pellicule which had its last soaking in STPP was practically devoid of apatite. It appeared similar to an unaltered sample of bacterial cellulose. The pellicule that had its last incubation in $CaCl_2$ was richly deposited with calcium phosphate. It is much whiter and thicker than the former pellicule.

Calcium hydroxide can be used as a calcium donor. Three-6 cm pellicules derived from a culture of *Gluconacetobacter hansenii* in Schramm-Hestrin media were cleaned in hot water, 1% SDS/1% NaOH solution. One pellicule was reserved as a control. Two pellicules were suspended in 100 mL of 12 mM $Ca(OH)_2$ for 1 day, and then added to 100 mL of 60 mM $Na_2HPO_4$. Precipitation was immediately observed. The cellulose went through 2 additional daily cycles of 12 mM $Ca(OH)_2$ alternated with 2 daily cycles of 60 mM $Na_2HPO_4$. The precipitated sample was significantly whiter, stiffer, and thicker than the control. One of the precipitated samples was dried and weighed while the other was stained with alizarin red S for calcium detection. The weight of the precipitated pellicule was 0.110 g while the unaltered pellicule was 0.0329 g.

Example 7

Apatite Formation in Phosphorylated Cellulose

Phosphate groups were chemically attached to the bacterial cellulose using a phosphorylation process. Precipitation occurred when the phosphorylated cellulose was incubated in salt solutions. This improved the mechanical properties of the composite and its ability to retain its shape.

Five 6-cm pellicules derived from a culture of *Gluconacetobacter hansenii* in Schramm-Hestrin media were cleaned in a hot water, 1% SDS/0.5% NaOH solution. The volume of the pellicules was approximately 38.7 mL, derived from weight. The pellicules were incubated for one day in 45% urea, and incubated for another day in a fresh solution of 45% urea, making their concentration about 41% urea. The pellicules were then incubated in a 42% phosphoric acid/75% urea solution until the pellicules had an approximate concentration of 31% phosphoric acid/53% urea. They were then put in a 120° C. oven for 3 hours, and then rinsed in nanopure water.

One of the phosphorylated pellicules was incubated in 100 mM $CaCl_2$ for 2 weeks (solution was changed 8 times). Precipitation was evident. The cellulose became whiter, denser, and more robust after incubation. The sample was put on a gel-dryer for 30 minutes. Its weight was found to be 0.0292 g. A control sample of phosphorylated cellulose that was not incubated was also dried for comparison. Due to its poor mechanical properties and thin composition, however, it was unable to be fully recovered from the gel-dryer. This further proves the strengthening behavior of incubating the phosphorylated cellulose in salt solutions.

A sample of phosphorylated bacterial cellulose prepared in the above-described procedure was incubated in simulated body fluid for 12 days. The solution was changed 7 times. After treatment, the cellulose was more robust, durable, and had a slight white precipitate. The sample is put on a gel-dryer for 30 minutes. Its weight was found to be 0.0309 g.

A sample of phosphorylated bacterial cellulose was incubated in saturated calcium hydroxide (about 12 mM) for 9 days (solution was changed 5 times). As with the above-described solutions, the cellulose became more robust and durable. But unlike the above-described solutions, calcium hydroxide produced significantly more white precipitate in the matrix. The sample was put on a gel-dryer for 30 minutes. Its weight was found to be 0.0166 g.

Soaking of the phosphorylated bacterial cellulose in this combination of solutions produced the most precipitate. A sample of phosphorylated bacterial cellulose was incubated in saturated calcium hydroxide (about 12 mM) for 9 days (solution was changed 5 times). Subsequently, the sample was incubated in simulated body fluid for 9 days (the solution was changed 5 times). The precipitate was more abundant and whiter than the sample incubated in calcium hydroxide alone. The sample was put on a gel-dryer for 30 minutes. Parching the sample caused it to become much more brittle and white with apatite. The weight was found to be 0.0772 g.

Example 8

Incorporation of Other Calcium Salts

Additional immersion solutions were investigated to see if other calcium salts, such as calcium fluoride and calcium carbonate, could be integrated into bacterial cellulose. Because physiological hydroxyapatite possesses strains of fluoride and carbonate, using these solutions may be utilized to produce a more biomimetic ceramic. Fluoride is known to be beneficial to dental implants due to its ability to inhibit cavities.

A 6-cm bacterial cellulose pellicule derived from *Gluconacetobacter hansenii* grown in Schramm-Hestrin media was cleaned in a hot water, 1% SDS/0.5% NaOH solution. The pellicule was soaked in 100 mL of 100 mM $CaCl_2$ for one day, then soaked in 100 mL of 200 mM KF. Precipitation was immediately observed. The pellicule was incubated for 2 more daily cycles of $CaCl_2$ alternated with 2 daily cycles of KF. The cellulose became very white and thick with precipitate. After drying, its weight was measured to be 0.2496 g. The identification of the salt is suspected to be calcium fluoride.

In another experiment, two 10-cm bacterial cellulose pellicules from *Gluconacetobacter hansenii* grown on synthetic glucose media were cleaned with hot water and 1% sodium hydroxide. The pellicules were soaked in 100 mL of 100 mM $CaCl_2$ for one day, then soaked in 100 mL of 100 mM $Na_2CO_3$. Precipitation was immediately observed. The pellicules were incubated for 2 more daily cycles of $CaCl_2$ alternated with 2 daily cycles of $Na_2CO_3$. When placed into acetic acid, an effervescent reaction was observed indicating that the salt in the matrix might be calcium carbonate.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of tissue repair within the body of animals, comprising the steps of:
   providing a composite biocompatible hydrogel material comprising a porous polymer matrix and a calcium salt, said polymer matrix comprising a plurality of pores and providing a Young's modulus of at least 10 GPa, and said calcium salt disposed in at least some of said pores, and
   inserting said hydrogel material into cartilage or bone tissue of an animal, wherein said hydrogel material supports cell colonization in vitro for autologous cell seeding, wherein said polymer comprises bacterial cellulose, and wherein said calcium salt consists essentially of calcium deficient hydroxyapatite disposed in said matrix in the form of crystals.

2. The method of claim 1, wherein said hydrogel material consisting essentially of bacterial cellulose, calcium salt, and at least one of bone morphogenetic proteins (BMP's) or chondrocytes, wherein said bacterial cellulose provides a porous matrix, said calcium salt consists essentially of calcium deficient hydroxyapatite disposed in said matrix in the form of crystals, and said at least one of bone morphogenetic proteins (BMP's) or chondrocytes is disposed in said matrix.

* * * * *